United States Patent [19]

Flemer, III

[11] Patent Number: Plant 7,217

[45] Date of Patent: Apr. 10, 1990

[54] *ACER PALMATUM* "CRIMSON PRINCE"

[75] Inventor: William Flemer, III, Princeton, N.J.

[73] Assignee: Newplant Associates, Princeton, N.J.

[21] Appl. No.: 206,411

[22] Filed: Jun. 13, 1988

[51] Int. Cl.[4] ..... A01H 5/00

[52] U.S. Cl. ..... Plt./51

[58] Field of Search ..... Plt./51

[56] References Cited

PUBLICATIONS

Vertrees, J. D., "*A. palmatum* 'Atropurpureum Superbum'", *Japanese Maples,* Timber Press, Forest Grove, Ore., p. 47.

*Primary Examiner*—James R. Feyrer

*Attorney, Agent, or Firm*—Frank B. Robb

[57] ABSTRACT

A seedling of the variety *Acer palmatum* "Bloodgood" (an unpatented variety) noticeable for its vigorous growth, deeper red color in the summer, greater height of growth as compared with other "Bloodgood" seedlings of the same age, cold hardiness and non-susceptibility to tip die-back of the summer growth, from cold winters.

2 Drawing Sheets

This invention relates to a new variety of *Acer palmatum* tree discovered as a seedling in a block of red foliaged *Acer palmatum* Bloodgood trees and noticeable for its deeper red color of summer growth.

In the course of growing and breeding decorative trees in a program carried on by me in a nursery near Princeton, N.J., I have been careful to watch for and select seedlings in large blocks of trees which are clearly different from and have better characteristics than the other trees in the block.

Thus the instant variety was selected for its characteristics which make it outstanding from the trees in the same variety which in this instance is an *Acer palmatum* known as the variety "Bloodgood" (an unpatented variety).

Particularly noticeable when first observed was the deeper red color in the summer months, which led to the selection of the commercial designation "Crimson Prince" for the tree of my new variety.

My new variety is twice as vigorous and rapid a grower as *Acer palmatum* 'Atropurpureum' grown under identical conditions in adjacent rows and blocks. My new variety is noticeably more cold hardy then 'Atropurpureum' and does not exhibit twig die back during cold winters.

I have determined that the branching habit of the plant is upright with narrow crotches (at approximately 15 degree angles to the trunk) in young trees. As the plant matures the terminal portions of the branches spread to give a broad outline with the tips or small twigs of lower branches becoming moderately pedulous. The mature tree is densely branched.

I note that in considering the flowers we find they are inconspicuous and reddish purple in color, borne in clusters of 8 to 12 flowers per corymb. They are perfect and 0.8 cm (8 mm) across.

As for the seeds, they are paired winged samaras, each samara being about 2.5 cm. long. The pedicle is about 1.4 cm. long and the total length of the corymb is about 10 to 11 cm.

The samara wings are Deep Purplish Red — 10 RP3/10 in the late spring and summer, later turning medium brown before falling. The seeds and samaras ripen and fall in a normal year about October 10 to 15.

While it might be helpful to compare my new variety with *Acer palmaturm* 'superbum' leaves, I do not have any of the same available for comparison and can only present the leaf color previously described. It is my belief that 'superbum' only exists in a few European Arboreta and is not currently grown in the nursery trade.

Continued asexual reproduction by me of the variety by grafting on *Acer palmatum* seedlings, has shown that the deeper red color persists and other distinctions such as stronger growth, taller and broader by one third, than "Bloodgood" grafts of the same age, as well as greater cold hardiness, all continued from generation to generation and are fixed valuable distinctions.

In addition it has been observed that considerably less tip die-back of previous summer growth, results with my new variety, all the foregoing characteristics being valuable for obvious commercial reasons.

BRIEF DESCRIPTION OF THE DRAWING

In the accompanying drawing, in FIG. 1 there is shown a typical tree of my new variety which illustrates the previously described characteristics and particularly discloses the color as nearly as can be done by an illustration of this kind, the color references where used in the following detailed description being compared with the Munsell Color Fan supplied by Munsell Color Company of Baltimore, Md., the disclosure being as accurate as possible to supply by photographic processes used.

Figure 1:
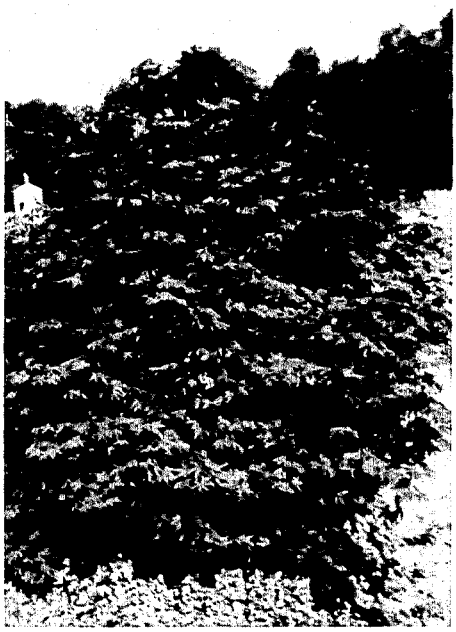
Figure 2:
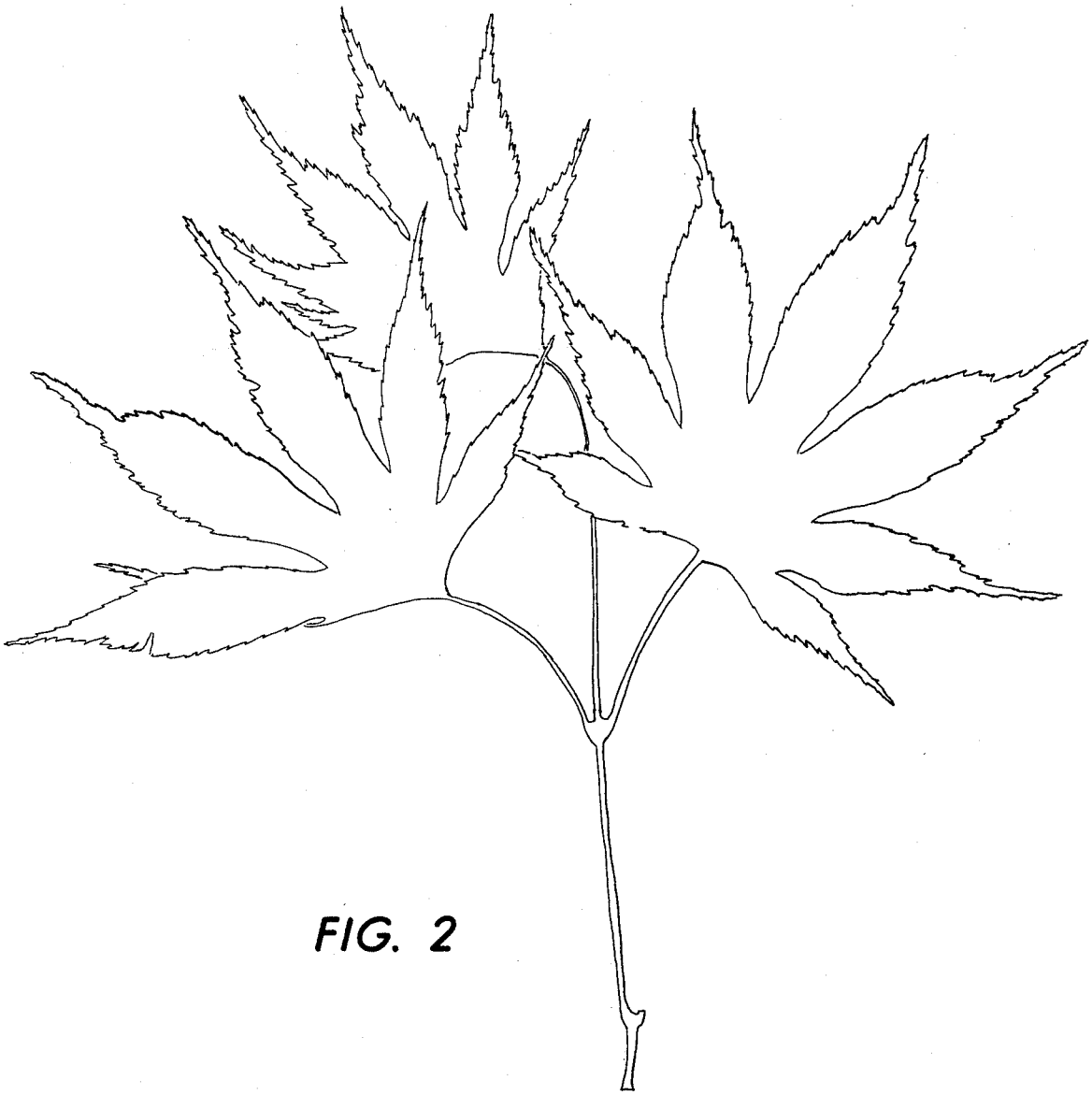
In FIG. 2 there is disclosed in outline leaves on a stem to show the configurations of the same along with the stem shape and in approximately full size black and white, understanding that this is purely and simply intended to be a diagrammatic disclosure.

Common color designations where used are applicable, and have the ordinary significance which may apply in a description of a tree of this kind as used herein.

DETAILED DESCRIPTION

Parentage:

*Seed parent.*—*Acer palmatum* "Bloodgood" (unpatented).

*Pollen parent.*—*Acer palmatum* atropurpureum.

Tree: Small; spreading; dense; hardy.

*Trunk.*—Stocky; smooth.

*Branches.*—Slender; smooth. Color — Very dark red 2.5R 2/2.

*Lenticels.*—Sparse; minute. Number — 4 to 6 cm of stem.

*Bark.*—Older branches — smooth; medium grey color. Young trees — smooth; dark red 2.5R3/7.

*Leaves.*—Quantity — Abundant. Length — 13 to 14 cm. Width — 12 to 14 cm. Shape — Palmate; deeply incised; doubly serrate; 5 to 7 lobed; sub cordate at base. Summer color — upper surface: Dark red 2.5R 3/7. Under surface: dark greenish red. Fall color — Strong red 5R 4/12. Margin — Doubly serrate. Petiole — Medium; 3 to 4 cm. long. Glands — None.

*Flower buds.*—Not significant. Inconspicious — same in dormant state as when they produce leafy shoots.

*Flowers.*—Not significant. Borne in small, smooth stemmed clusters — purple — 6.5 mm across.

*Petalage.*—Not significant.

*Samara.*—Not significant. 3 to 5 flowers per cluster; anthers smooth — not pubescent.

*Fruits.*—Winged samaras, 2 cm long, borne in opposite pairs, not discernably different in a dormant state from buds which will produce leafy shoots.

I claim:

1. An *Acer palmatum* tree substantially as herein shown and described, characterized particularly as to novelty by its deeper red summer color, stronger growth, growing one third taller and broader than sister "Bloodgood" grafts of the same age, greater cold hardiness than other purple leafed *Acer palmatum* clones and resistance to injury by cold winters as compared with other clones than suffer from considerable tip die-back of a previous summer's growth.

* * * * *